United States Patent [19]

Meilland

[11] Patent Number: Plant 6,087

[45] Date of Patent: Jan. 26, 1988

[54] ROSE PLANT—MEIKROTAL VARIETY

[75] Inventor: Marie-Louise Meilland, Antibes, France

[73] Assignee: The Conard-Pyle Company, West Grove, Pa.

[21] Appl. No.: 767,784

[22] Filed: Aug. 20, 1985

[51] Int. Cl.[4] ..... A01H 5/00

[52] U.S. Cl. ..... Plt./1

[58] Field of Search ..... Plt. 1, 28

*Primary Examiner*—Robert E. Bagwill

*Attorney, Agent, or Firm*—Burns, Doane, Swecker & Mathis

[57] ABSTRACT

A new and distinct variety of rose plant is provided which forms attractive semi-double blossoms which are cherry red on the upper surface and carmine pink on the under surface. The plant forms in abundance dark glossy foliage and exhibits an arching growth habit which renders it highly suited for use as a ground cover. Good hardiness and resistance to fungal diseases are manifest. The new variety can be readily propagated from cuttings.

16 Drawing Figures

SUMMARY OF THE INVENTION

The new variety of ground cover rose plant was created by artificial pollination wherein two parents were crossed which previously had been studied in the hope that they would contribute the desired characteristics. The female parent (i.e., the seed parent) of the new variety was the variety Meitiraca. The male patent (i.e., the pollen parent) of the new variety was the variety Meimont. The parents of the new vareity are nonpatented in the United States. The parentage of the new variety can be summarized as follows:

Meitiraca × Meimont.

The seeds resulting from the above pollination were sown and 22 plantlets were obtained which were physically and biologically different from each other. Selective study resulted in the identification of a single plant of the new variety.

It was found that the new variety of ground cover rose plant of the present invention possesses the following combination of characteristics:

(a) forms attractive semi-double blossoms which are cherry red on the upper surface and carmine pink on the under surface,
(b) forms in abundance dark glossy foliage,
(c) exhibits an arching growth habit which forms a plant having a greater width than height,
(d) exhibits good hardiness, and
(e) exhibits good resistance to fungal diseases.

The new variety meets the needs of the horticultural industry for many usages. It is particularly well-suited when grown en masse for use as an attractive, dense, and low-growing ornamental ground cover in parks, gardens, and residential and commercial landscapes. The dark glossy leaves in combination with the bright flowers provide a strikingly noteworthy appearance.

The new variety has been found to undergo asexual propagation by a number of routes, including budding, grafting, use of cuttings, etc. The new variety propagates well from cuttings and readily forms its own roots. The characteristics of the new variety have been found to be strictly transmissible by such asexual propagation from one generation to another.

The new variety has been named the Meikrotal variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were grown at LeLuc, France.

DETAILED DESCRIPTION

Figures 1, 2, 3, 4, 5, 6, 7, 8, 9, 10, 11, 12, 13, 14, 15, 16:
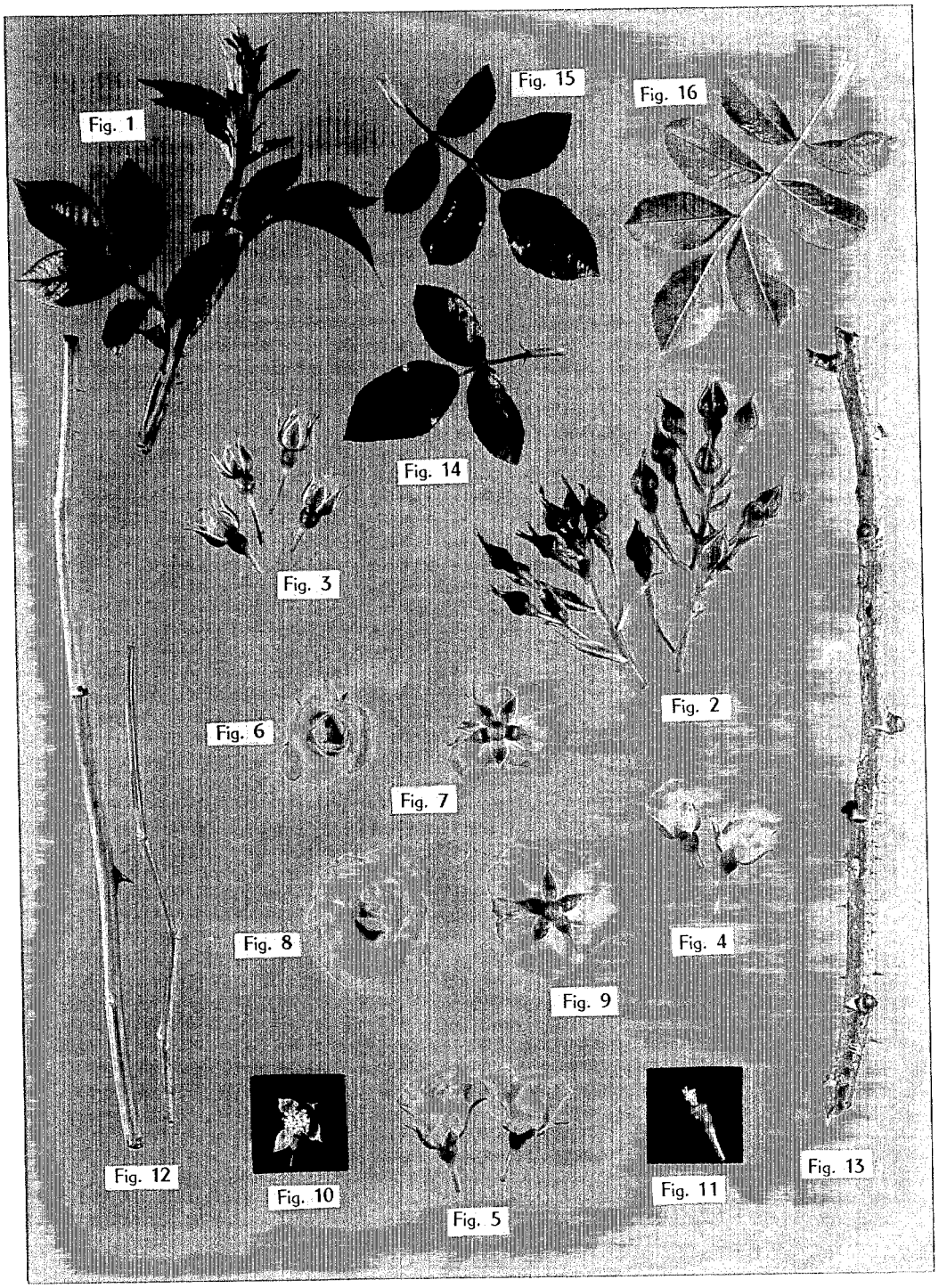
FIG. 1 illustrates a specimen of a young shoot.
FIG. 2 illustrates two clusters of flowering buds before the opening of the sepals.
FIG. 3 illustrates specimens of four flowering buds at the opening of the sepals.
FIG. 4 illustrates specimens of two flowering buds at the opening of the petals.
FIG. 5 illustrates specimens of two flowers in the course of opening.
FIG. 6 illustrates a specimen of a partially open flower—plan view—obverse.
FIG. 7 illustrates a specimen of a partially open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of two flowering stems.
FIG. 13 illustrates a specimen of a main branch.
FIG. 14 illustrates a specimen of a leaf with three leaflets—upper surface.
FIG. 15 illustrates a specimen of a leaf with five leaflets—upper surface.
FIG. 16 illustrates a specimen of a leaf with seven leaflets—under surface.

The chart used in the identification of the colors is that of The Royal Horticultural Society (R.H.S. Colour Chart). The description is based on three-year old specimens of the new variety during June while growing outdoors on their own roots in field soil at LeLuc, France.

Class: Ground cover.

Plant:

*Height.*—Approximately 1.5 to 1.7 meter.

*Habit.*—Arching growth habit which produces a plant having a greater width than height.

Branches:

*Color.*—Young stems: reddish brown. Adult wood: Yellow-Green Group 146B.

Leaves:

*Petioles.*—Upper surface: reddish brown on young foliage and light green on adult foliage. Under surface: light green.

*Leaflets.*—Number: 3, 5, and 7 (most often). Shape: elliptic. Serration: simple and regular. General appearance: dark and glossy. Color (young foliage): Upper surface: Yellow-Green Group 146B. Under surface: Yellow-Green Group 146C. Color (adult foliage): Upper surface: Yellow-Green Group 146A. Under surface: Yellow-Green Group 146B.

Inflorescence:

*Number of flowers.*—Approximately 2 to 18 per stem.

*Peduncle.*—Its length is approximately 3 cm. on average.

*Buds.*—Shape: oval. Length: approximately 1.5 cm. on average. Color upon opening: Upper surface: Red Group 45C. Under surface: Red Group 45B and lighter toward the petal base.

*Flower.*—Diameter: approximately 3.7 cm. on average. Color (when opening begins): Upper surface: Red Group 45C bordered with a light suffusion of Red Group 45B and with a small white eye at the base of the petal. Under surface: Red Group 52A. Color (when partially open): Upper surface: Red Group 45C bordered with a light suffusion of Red Group 45B and with a small white eye at the base of the petal. Under surface: Red Group 52A passing to Red Group 52B and slightly whitish at the base. Color (at end of opening): Upper surface: Red Group 45C passing to Red Group 45D at the center of the petal and with a white base. Under suface: Red Group 52A passing to Red Group 52B and slightly whitish at the base. Fragrance: none. Lasting quality: long. Petal number: approximately 15 to 20. Stamen number: approximately 78 on average. Pistils: approximately 15 on average.

Development:

*Hardiness.*—Very good.

*Disease resistance.*—Extremely resistant to the major fungal diseases which commonly attack roses.

I claim:

1. A new and distinct variety of ground cover rose plant characterized by the following combination of characteristics:

(a) forms attractive semi-double blossoms which are cherry red on the upper surface and carmine red on the under surface, (b) forms in abundance dark glossy foliage, (c) exhibits an arching growth habit which forms a plant having a greater width than height, (d) exhibits good hardiness, and (e) exhibits good resistance to fungal diseases;

substantially as herein shown and described.

* * * * *